United States Patent [19]

Esteve Subirana et al.

[11] 4,216,214
[45] Aug. 5, 1980

[54] 4-TERT. BUTYL-3'-CHLORODIPHENYLAMINE DERIVATIVES, THEIR PREPARATION AND THEIR APPLICATION AS ANTI-HISTAMINIC DRUGS

[75] Inventors: Antonio Esteve Subirana; Jose Esteve Soler, both of Barcelona, Spain

[73] Assignee: PRODESIN (Productos Esteve Internacional S.A.), Barcelona, Spain

[21] Appl. No.: 864,781

[22] Filed: Dec. 27, 1977

[30] Foreign Application Priority Data

Jan. 4, 1977 [FR] France ................... 77 00051

[51] Int. Cl.$^2$ ................ C07D 295/12; A61K 31/535; A61K 31/495; A61K 31/435
[52] U.S. Cl. ........................ 424/244; 260/239 B; 260/326.05; 260/570.5 P; 544/165; 544/402; 546/229; 424/248.56; 424/250; 424/267; 424/274
[58] Field of Search ............ 260/326.85, 239 B, 570.5; 546/229; 544/402, 165; 424/244, 267, 274, 248.56, 250

[56] References Cited

U.S. PATENT DOCUMENTS 2,739,984   3/1956   Hafliger .................. 260/570.5 D

OTHER PUBLICATIONS

King et al., Chem. Abs. 40, 2805$^7$ (1946).

Primary Examiner—Mark L. Berch
Attorney, Agent, or Firm—Dressler, Goldsmith, Shore, Sutker & Milnamow, Ltd.

[57] ABSTRACT

Novel derivatives of formula (I) and the pharmaceutically acceptable salts thereof.

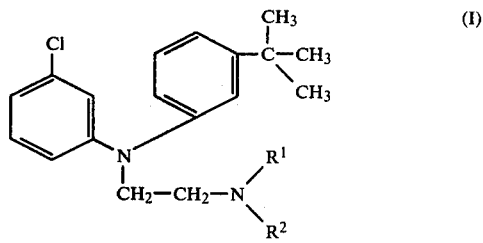

wherein $R^1$ and $R^2$ are the same or different and each is a lower alkyl group, or $R^1$ and $R^2$ together with the nitrogen atom to which they are attached, form a saturated heterocyclic group optionally containing, in addition to the said nitrogen atom, a second hetero atom, a process for the preparation thereof, and their use as anti-histamine anti "$H_2$" agents.

11 Claims, No Drawings

4-TERT. BUTYL-3'-CHLORODIPHENYLAMINE DERIVATIVES, THEIR PREPARATION AND THEIR APPLICATION AS ANTI-HISTAMINIC DRUGS

The present invention relates to 4-tertiary, butyl-3'-chlorodiphenylamine derivatives and their pharmaceutically acceptable acid-addition salts having anti-histamine ($H_1$ and $H_2$ receptors) and gastric anti-secretory action, the use of these compounds as drugs, and a process for the preparation thereof.

The present invention provides in one aspect novel derivatives of general formula (I) and the pharmaceutically acceptable acid addition salts thereof,

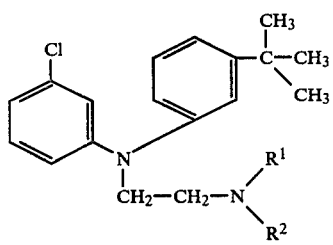

wherein $R_1$ and $R_2$ are the same or different and each is a lower alkyl group, or $R^1$ and $R^2$ together with the nitrogen atom to which they are attached form a saturated heterocyclic group optionally containing, in addition to the said nitrogen atom, a second hetero-atom.

Preferred compounds according the the present invention are those of general formula 1 in which $R_1$ and $R_2$ are straight chain lower alkyl groups with from 1 to 4 carbon atoms, most preferably 1 or 2 carbon atoms. Compounds of general formula (I) wherein $R_1$ and $R_2$ are identical are particularly preferred.

Other preferred derivatives according to the present invention are those of formula 1 wherein the saturated heterocyclic group formed by $R_1$ and $R_2$ together with the nitrogen atom is selected from the group consisting of pyrrolidine, piperidine, piperazine, morpholine and perhydroazephine. From these latter preferred compounds it may seem that if the saturated heterocyclic ring contains a second hetero-atom, it is preferential that it be selected from the group consisting of oxygen and nitrogen. The pharmaceutically acceptable acid addition salts of the 4-tertiary butyl-3'-chlorodiphenylamine derivatives of formula (I) are prepared by reaction of a derivative of formula (I) with a non-toxic acid. Non-toxic acids which are acceptable from the pharmaceutical point of view include, for example, hydrochloric acid, hydrobromic acid, sulphuric acid, phosphoric acid, acetic acid, maleic acid, fumaric acid, oxalic acid, lactic acid, tartaric acid, citric acid, gluconic acid, saccharic acid and paratoluene sulphonic acid.

The present invention also provides a process for the preparation of the derivatives of formula I, said process which comprises the step of reacting 4-tertiary butyl-3'-chlorodiphenylamine or one of the alkali metal or alkaline earth metal salts thereof with a beta-halogenated derivative of ethyl amino formula (II)

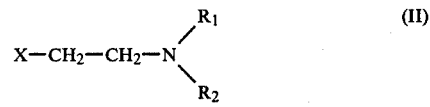

wherein X is a halogen atom and $R_1$ and $R_2$ are as hereinbefore defined.

For the preparation of the derivatives of formula I of the present invention from alkali metal or alkaline earth metal salts of 4-tertiary butyl-3'-chlorodiphenylamine, the sodium salt is conveniently used. This may itself be formed by adding sodium hydride or sodium amide to the reaction medium which is subsequently heated. The reaction medium is not critical, it being sufficient for the solvent used to simply be inert towards the starting compounds and the end products formed. In practice, an anhydrous dioxane medium is preferred. The reaction with the beta halogenated derivative of ethyl amine, for example with the chlorinated derivative, may be carried out conveniently at a temperature of from 70° to 80° C. but it should be noted that this reaction temperature is not critical.

When carrying out the process of the present invention the derivative according to the present invention is obtained in the form of a free base by precipitation or elimination of the solvent under reduced pressure. If derivatives of formula I are to be obtained in the form of their pharmaceutically acceptable acid addition salts, these may be obtained in a conventional manner by adding a suitable acid to solvent such as, for example, isopropyl alcohol and by subsequently precipitating the compound formed with for instance, anhydrous ethyl ether.

The present invention will now be illustrated by means of particular examples selected from the preferred 4-tertiary butyl-3'-chlorodiphenylamine derivatives according to the invention, but they should not be constructed as limiting the invention to the specific procedure described therein.

EXAMPLE 1

Preparation of N-(2-piperidino-ethyl)-4-tertiary butyl-3'-chlorodiphenylamine 1.44 g (30 mmoles) of sodium hydride (50% dispersion in oil) are added to a solution of 6.7 g (25 mmoles) of 4-tertiary-butyl-3'-chlorodiphenyl amine in 50 ml of anyhydrous dioxane and the mixture is heated with stirring at 70° C. for six hours. The reaction medium is then left to cool and 3.5 g (25 mmoles) of 2-piperidino-ethyl chloride are added to the reaction medium with stirring at 70° C. for 12 hours.

The mixture is then left at ambeint temperature for 24 hours and is subsequently poured on to ice-water and extracted with ethyl ether. The ether solution is then washed with water and the mixture extracted with 4 N hydrochloric acid. The hydrochloric solution is washed with ether and is alkalized with sodium carbonate (2 N). The sodium carbonate solution is extracted with ethyl ether, washed with water until neutrality is reacted and the mixture is dried on anhydrous sodium sulphate. The mixture is filtered and dry evaporated to yield an oil which is then dissolved in petroleum ether and the resulting solution is subsequently passed over a column of alumina. The mixture is dry evaporated and the oil obtained is dissolved in isopropanol. This alcohol solution is subsequently purified by addition of hot active carbon followed by filtration. The mixture is exactly neutralized using concentrated hydrochloric acid and the product is precipitated by addition of anhydrous ethyl ether. The salt obtained is recrystallized by filtration with a mixture of ethanol and ethyl ether (1:3). 7.9 g of N-(2-piperidinoethyl)-4-tertiary-butyl-3'-chlorodiphenylamine are obtained as a white product having a melting point of between 221° and 224° C.

The yield is 80% of theoretical.

|  | C | C | Cl | N |
|---|---|---|---|---|
| Calculated | 67.80 | 7.91 | 17.40 | 6.87 |
| Found | 67.78 | 7.87 | 17.43 | 6.91 |

EXAMPLES 2 TO 5

The derivatives mentioned in table 1 below may be prepared from 4-tertiary-butyl-3'-chlorodiphenyl amine and the corresponding beta chlorinated derivative of ethyl amine by a process analogous to the one described in Example 1.

TABLE I

| Example No. | $-N\begin{matrix}R_1\\R_2\end{matrix}$ | Melting Point | Empirical Formula | Yield in % | Analysis (%) C | H | Cl | N |
|---|---|---|---|---|---|---|---|---|
| 2 | —N(CH$_3$)$_2$ | 173°–177° C. | C$_{20}$H$_{27}$ClN$_2$ . HCl | 73% Calculated | 65.39 | 7.68 | 19.30 | 7.62 |
|  |  |  |  | Found | 65.43 | 7.65 | 19.19 | 7.58 |
| 3 | —N(C$_2$H$_5$)$_2$ | 188°–191° C. | C$_{22}$H$_{31}$ClN$_2$ . HCl | 80% Calculated | 66.82 | 8.15 | 17.93 | 7.08 |
|  |  |  |  | Found | 66.78 | 8.11 | 17.97 | 7.11 |
| 4 |  | 196°–199° C. | C$_{22}$H$_{29}$ClN$_2$ . HCl | 75% Calculated | 67.16 | 7.68 | 18.03 | 7.12 |
|  |  |  |  | Found | 67.13 | 7.64 | 18.09 | 7.05 |
| 5 |  | 225°–228° C. | C$_{24}$H$_{33}$ClN$_2$ . HCl | 63% Calculated | 68.39 | 8.13 | 16.82 | 6.64 |
|  |  |  |  | Found | 68.29 | 8.07 | 16.85 | 6.67 |

The derivatives of formula (I) and their pharmaceutically acceptable acid-addition salts have an anti-histamine action and chiefly inhibit the effects of histamine at the level of the so-called "H$_2$" receptor sites, (i.e. those which have, for example, an effect on the secretion of gastric acid) and inhibit very slightly the effects of histamine at the level of the so-called "H$_1$" receptor sites (i.e. those which, for example, have an effect on the contraction of the intestine).

The pharmacological properties of the derivatives forming the subject of the present invention have been demonstrated in the following manner:

(1) Gastric anti-secretory action

Sprague-Dawley rats having a body weight of from 300 to 350 g are used for studying the antagonistic action of the "H$_2$" histamine receptor sites by the method described by Ghosh and Schild (1958). The gastric secretion is stimulated by intravenous injection of constant doses of histamine (2.5 μmoles/kg) or of carbachol (5 nmoles /kg). The gastric anti-secretory action is then determined by the intravenous dose (in μmole/kg) of derivative which inhibits by 50% the effect caused by the histamine or carbachol (DI-50). Some of the results obtained for three particular derivatives according to the invention are shown in table II by way of example.

TABLE II

| Derivative of formula (I) | DI-50 with histamine | DI-50 with carbachol |
|---|---|---|
| N-(2-pyrrolidinoethyl)-4-tert.butyl-3'-chlorodiphenylamine | 2.2 | 20 |
| N-(piperidinoethyl)-4-tert.butyl-3'-chlorodiphenyl amine | 1.0 | >20 |
| N-(2-diethylaminoethyl)-4-tert.butyl 3'-chlorodiphenyl amine | 6.0 | >20 |

(2) Test on isolated organ

During this test, the products are added to the bath in an aqueous solution. The interaction of the various products is determined with different antagonists: Histamine, acetyl choline, serotonine and norepinephrine.

The antagonists are employed in constant doses to produce contractions in the various biological reactants described below in table III.

TABLE III

| Agonists | Concentration of Agonist μ | Biological Reactant | Cl-50 of products Product I | Product II | Prod. III |
|---|---|---|---|---|---|
| Histamine | 0.05 | Ileum of Guinea Pig | 19.83 | 2.25 | 27.85 |
| Acetyl Choline | 0.05 | Ileum of Guinea Pig | 25.4 | 25.5 | 25.3 |
| Seratonine | 0.10 | Uterus of Rat | 0.05 | 0.38 | 2.60 |
| Norepinephrine | 1.0 | Deferent of Rat | 25.4 | 24.5 | 25.0 |

Product I: N-(2-pyrrolidinoethyl)-4-tert.butyl-3'-chlorodiphenylamine
Product II: N-(2-piperidinoethyl)-4-tert.butyl-3'-chlorodiphenylamine
Product III: N-(2-diethylaminoethyl)-4-tert.butyl-3'-chlorodiphenylamine The micromolar concentration which inhibits 50% of the response produced by the constant concentration of each agonist (Cl-50) is determined for each derivative. The results are showm in Table III.

(3) Action on hypotension produced by histamine in rats.

The action of the products according to the present invention for blocking transitory hypotension induced by histamine (0.125 μmole/kg) was studied on anaesthetized rats. The derivatives according to the present invention have a very weak "$H_1$" antihistamine action in comparison with the action of prometazine. Furthermore, the action against carbachol, acetyl choline, seratonine and norepinphrine is practically negligible. Conversely, the action on the "$H_2$" receptor site is considered as very significant because all the derivatives of formula (I) and their pharmaceutically acceptable acid-addition salts have an action in doses of less than or equal to 6 μmoles/kg.

(4) Toxicity (a) Acute toxicity in mice

The lethal dose 50 (LD-50) of various derivatives administered orally and intra-peritoneally to mice weighing between 20 and 25 g was determined. The results obtained are shown in Table IV below.

TABLE IV

| Derivative | LD-50 mg/kg | Orally μMoles/kg | LD-50 i.p. mg/kg | μMoles/kg |
|---|---|---|---|---|
| N-(2-pyrrolidino-ethyl)-4-tert. butyl-3'-chloro-diphenylamine | 3000 | 7625 | 155 | 390 |
| N-(2-piperidino-ethyl)-4-tert. butyl-3'-chloro-diphenylamine | >3500 | >8500 | 1000 | 2454 |
| N-(2-diethylamino-ethyl)-4-tert. butyl-3'-chloro diphenylamine | >6000 | >15000 | 395 | 1000 |

(B) Acute toxicity in rats

The acute toxicity was determined by oral means in Sprague-Dawley rats having a body weight of 150 to 180 g. The LD-50 of N-(2-piperidinoethyl)-tertiary-butyl-3'-chlorodiphenylamine hydrochloride by the oral route in rats is above 3500 mg/kg.

(C) Sub-Acute Toxicity by oral means with rats

Three batches of Sprague-Dawley rats each consisting of six males and six females were used. N-(2-piperidinoethyl)-4-tertiary-butyl-3'-chlorodiphenylamine hydrochloride was administered orally to the first two batches in doses of 200 mg/kg and 50 mg/kg respectively. The third batch received a zero dose (distilled water) and was thus used as a control. All urine and hematological analyses were normal at the beginning and at the end of the experiments as was the weekly weight control. The mortality rate observed was 8.33% with the 50 mg/kg dose and 33% with the 200 mg/kg dose.

Moreover, anatomopathological examination did not reveal a lesion which could be attributed to the derivatives administered.

Taking into consideration the valuable pharmacological properties of the derivatives forming the subject of the present invention, they may therefore be used very advantageously as anti-$H_2$anti-histamine agents in human and/or veterinary medicine.

Consequently, the derivatives forming the subject of the present invention may be used for treating gastro-duodenal illnesses such as ulcers of the stomach, Zellinger-Ellison syndromes, gastric haemorrhages and gastric ulcers.

In human therapeutics, the proposed dose of the derivatives according to the present invention is between about 100 and 300 mg per day, administered, for example, in the form of tablets or gelatin-coated pills. It should be noted that other conventional means of administration such as parenteral, for example intramuscular administration, may also be used.

We claim:

1. Compounds of formula I and the pharmaceutically acceptable acid addition salts thereof,

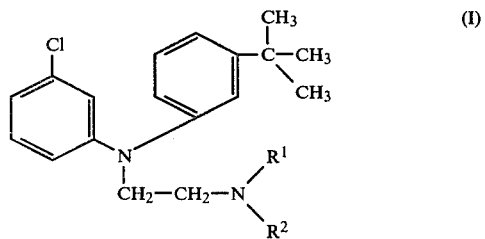

wherein $R_1$ and $R_2$ are the same or different and each is a lower alkyl group or $R^1$ and $R^2$ together with the nitrogen atom to which they are attached, form a saturated heterocyclic group selected from the group consisting of pyrrolidino, piperidine, piperazine, morpholine and perhydroazepine groups.

2. Compounds according to claim 1, wherein $R_1$ and $R_2$ are straight chain lower alkyl radicals with from 1 to 4 carbon atoms.

3. Compounds according to claim 1, wherein $R^1$ and $R^2$ are the same.

4. A pharmaceutical formulation for treatment of gastro-duodenal illnesses, consisting of an effective amount, at least one of the derivatives of formula (I) according to claim 1 as active ingredient in combination with a pharmaceutically acceptable carrier or diluent.

5. A method of treating gastro-duodenal illnesses which comprises administering an effective non-toxic amount of a pharmaceutical formulation according to claim 4 to the affected animal or human.

6. N-(2-piperidinoethyl)-4-tertiary-butyl-3'-chlorodiphenyl amine.

7. N-(2-dimethylaminoethyl)-4-tertiary-butyl-3'-chlorodiphenylamine.

8. N-(2-diethylaminoethyl)-4-tertiary butyl-3'-chlorodiphenylamine.

9. N-(2-pyrrolidinoethyl)-4tertiary butyl-3'-chlorodiphenylamine.

10. N-(2-perhydroazepinoethyl)-4-tertiary butyl-3'-chlorodiphenyl amine.

11. Compounds according to claim 1, wherein they are the hydrochloride salts.

* * * * *

UNITED STATES PATENT AND TRADEMARK OFFICE
CERTIFICATE OF CORRECTION

PATENT NO. : 4,216,214

DATED : August 5, 1980

INVENTOR(S) : Subirana et al.

It is certified that error appears in the above-identified patent and that said Letters Patent are hereby corrected as shown below:

Column 3, line 9, "The yield is 80% of theoretical" should not be a new paragraph.

Column 3, line 10, "Elemental Analysis for $C_{23}H_{31}ClN_2 \cdot HCl$" should appear as a heading just above the tabulation.

Column 3, line 12, the heading above the second column in the Table should be "H" instead of "C."

Column 5, line 32, the figure "390" should be moved to the right into the last column of the table.

Column 6, line 56, (first line of Claim 8) there should be a hyphen after "tertiary" and no space between the inserted hyphen and "butyl."

Column 6, line 58 (first line of Claim 9) there should be a hyphen between "4" and "tertiary."

Column 6, line 61 (first line of Claim 10) there should be a hyphen after "tertiary."

Signed and Sealed this

Seventeenth Day of March 1981

[SEAL]

Attest:

RENE D. TEGTMEYER

Attesting Officer

Acting Commissioner of Patents and Trademarks